United States Patent
Elomari

(10) Patent No.: US 7,495,144 B2
(45) Date of Patent: Feb. 24, 2009

(54) ALKYLATION PROCESS USING AN ALKYL HALIDE PROMOTED IONIC LIQUID CATALYST

(75) Inventor: Saleh Elomari, Fairfield, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 382 days.

(21) Appl. No.: 11/388,511

(22) Filed: Mar. 24, 2006

(65) Prior Publication Data

US 2007/0225538 A1    Sep. 27, 2007

(51) Int. Cl.
*C07C 2/60* (2006.01)
*C07C 2/62* (2006.01)

(52) U.S. Cl. .................. 585/724; 585/725; 585/727; 585/728

(58) Field of Classification Search .............. 585/724, 585/725, 727, 728
See application file for complete search history.

(56) References Cited

U.S. PATENT DOCUMENTS

| | | | | |
|---|---|---|---|---|
| 3,764,637 | A | * | 10/1973 | Lyon .................... 585/721 |
| 3,864,423 | A | * | 2/1975 | Chapman ................ 585/703 |
| 4,122,245 | A | | 10/1978 | Nardi et al. |
| 4,463,071 | A | | 7/1984 | Gifford et al. |
| 4,463,072 | A | | 7/1984 | Gifford et al. |
| 5,104,840 | A | | 4/1992 | Chauvin et al. |
| 5,731,101 | A | | 3/1998 | Sherif et al. |
| 6,028,024 | A | | 2/2000 | Hirschauer et al. |
| 6,096,680 | A | | 8/2000 | Park |
| 6,797,853 | B2 | | 9/2004 | Houzvicka et al. |
| 2004/0077914 | A1 | | 4/2004 | Zavilla et al. |
| 2004/0133056 | A1 | | 7/2004 | Liu et al. |

\* cited by examiner

*Primary Examiner*—Thuan Dinh Dang
(74) *Attorney, Agent, or Firm*—Susan M. Abernathy; Steven H. Roth

(57) ABSTRACT

A process for the production of a high quality gasoline blending components from refinery process streams by the alkylation of light isoparaffins with olefins using an ionic liquid catalyst is disclosed. The alkylation process comprises contacting a hydrocarbon mixture comprising at least one olefin having from 2 to 6 carbon atoms and at least one isoparaffin having from 3 to 6 carbon atoms under alkylation conditions, said catalyst comprising a mixture of at least one acidic ionic liquid and at least one alkyl halide. In one embodiment, the acidic ionic liquid is chloroaluminate ionic liquid prepared by mixing aluminum trichloride ($AlCl_3$) and a hydrocarbyl substituted pyridinium halide, a hydrocarbyl substituted imidazolium halide, trialkylammonium hydrohalide or tetraalkylammonium halide of the general formulas A, B, C and D, respectively,

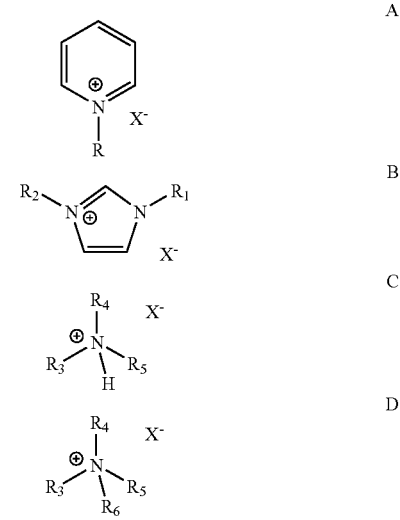

where R=H, methyl, ethyl, propyl, butyl, pentyl or hexyl group and X is a halide and preferably a chloride, and $R_1$ and $R_2$=H, methyl, ethyl, propyl, butyl, pentyl or hexyl group and where $R_1$ and $R_2$ may or may not be the same, and $R_3$, $R_4$, and $R_5$ and $R_6$=methyl, ethyl, propyl, butyl, pentyl or hexyl group and where $R_3$, $R_4$, $R_5$ and $R_6$ may or may not be the same.

15 Claims, No Drawings

ALKYLATION PROCESS USING AN ALKYL HALIDE PROMOTED IONIC LIQUID CATALYST

FIELD OF THE INVENTION

The present invention relates to a process for the alkylation of light isoparaffins with olefins using a catalyst comprising an ionic liquid and an alkyl halide.

BACKGROUND OF THE INVENTION

In general, conversion of light paraffins and light olefins to more valuable cuts is very lucrative to the refining industries. This has been accomplished by alkylation of paraffins with olefins, and by polymerization of olefins. One of the most widely used processes in this field is the alkylation of isobutane with $C_3$ to $C_5$ olefins to make gasoline cuts with high octane number using sulfuric and hydrofluoric acids. This process has been used by refining industries since the 1940's. The process was driven by the increasing demand for high quality and clean burning high-octane gasoline.

Alkylate gasoline is a high quality and efficient burning gasoline that constitutes about 14% of the gasoline pool. Alkylate gasoline is typically produced by alkylating refineries isobutane with low-end olefins (mainly butenes). Currently, alkylates are produced by using HF and $H_2SO_4$ as catalysts. Although these catalysts have been successfully used to economically produce the best quality alkylates, the need for safer and environmentally friendlier catalysts systems has become an issue to the industries involved.

The quest for an alternative catalytic system to replace the current environmentally unfriendly catalysts has been the subject of varying research groups in both academic and industrial institutions. Unfortunately, thus far, no viable replacement to the current processes has been put into practice at commercial refineries.

Ionic liquids are liquids that are composed entirely of ions. The so-called "low temperature" Ionic liquids are generally organic salts with melting points under 100 degrees C., often even lower than room temperature. Ionic liquids may be suitable for example for use as a catalyst and as a solvent in alkylation and polymerization reactions as well as in dimerization, oligomerization acetylation, metatheses, and copolymerization reactions.

One class of ionic liquids is fused salt compositions, which are molten at low temperature and are useful as catalysts, solvents and electrolytes. Such compositions are mixtures of components which are liquid at temperatures below the individual melting points of the components.

Ionic liquids can be defined as liquids whose make-up is entirely comprised of ions as a combination of cations and anions. The most common ionic liquids are those prepared from organic-based cations and inorganic or organic anions. The most common organic cations are ammonium cations, but phosphonium and sulphonium cations are also frequently used. Ionic liquids of pyridinium and imidazolium are perhaps the most commonly used cations. Anions include, but not limited to, $BF_4^-$, $PF_6^-$, haloaluminates such as $Al_2Cl_7^-$ and $Al_2Br_7^-$, $[(CF_3SO_2)_2N]^-$, alkyl sulphates ($RSO_3^-$), carboxylates ($RCO_2^-$) and many other. The most catalytically interesting ionic liquids for acid catalysis are those derived from ammonium halides and Lewis acids (such as $AlCl_3$, $TiCl_4$, $SnCl_4$, $FeCl_3$ . . . etc). Chloroaluminate ionic liquids are perhaps the most commonly used ionic liquid catalyst systems for acid-catalyzed reactions.

Examples of such low temperature ionic liquids or molten fused salts are the chloroaluminate salts. Alkyl imidazolium or pyridinium chlorides, for example, can be mixed with aluminum trichloride ($AlCl_3$) to form the fused chloroaluminate salts. The use of the fused salts of 1-alkylpyridinium chloride and aluminum trichloride as electrolytes is discussed in U.S. Pat. No. 4,122,245. Other patents which discuss the use of fused salts from aluminum trichloride and alkylimidazolium halides as electrolytes are U.S. Pat. Nos. 4,463,071 and 4,463,072.

U.S. Pat. No. 5,104,840 describes ionic liquids which comprise at least one alkylaluminum dihalide and at least one quaternary ammonium halide and/or at least one quaternary ammonium phosphonium halide; and their uses as solvents in catalytic reactions.

U.S. Pat. No. 6,096,680 describes liquid clathrate compositions useful as reusable aluminum catalysts in Friedel-Crafts reactions. In one embodiment, the liquid clathrate composition is formed from constituents comprising (i) at least one aluminum trihalide, (ii) at least one salt selected from alkali metal halide, alkaline earth metal halide, alkali metal pseudohalide, quaternary ammonium salt, quaternary phosphonium salt, or ternary sulfonium salt, or a mixture of any two or more of the foregoing, and (iii) at least one aromatic hydrocarbon compound.

Other examples of ionic liquids and their methods of preparation may also be found in U.S. Pat. Nos. 5,731,101; 6,797,853 and in U.S. Patent Application Publications 2004/0077914 and 2004/0133056.

In the last decade or so, the emergence of chloroaluminate ionic liquids sparked some interest in $AlCl_3$-catalyzed alkylation in ionic liquids as a possible alternative. For example, the alkylation of isobutane with butenes and ethylene in ionic liquids has been described in U.S. Pat. Nos. 5,750,455; 6,028,024; and 6,235,959 and open literature (*Journal of Molecular Catalysis*, 92 (1994), 155-165; "*Ionic Liquids in Synthesis*", P. Wasserscheid and T. Welton (eds.), Wiley-VCH Verlag, 2003, pp 275).

Aluminum chloride-catalyzed alkylation and polymerization reactions in ionic liquids may prove to be commercially viable processes for the refining industry for making a wide range of products. These products range from alkylate gasoline produced from alkylation of isobutane and isopentane with light olefins, to diesel fuel and lubricating oil produced by alkylation and polymerization reactions.

SUMMARY OF THE INVENTION

The present invention relates to an alkylation process comprising contacting a hydrocarbon mixture comprising at least one olefin having from 2 to 6 carbon atoms and at least one isoparaffin having from 3 to 6 carbon atoms with a catalyst under alkylation conditions, said catalyst comprising a mixture of at least one acidic ionic liquid and at least one alkyl halide. In one embodiment, the acidic ionic liquid is a chloroaluminate ionic liquid prepared by mixing aluminum trichloride ($AlCl_3$) and a hydrocarbyl substituted pyridinium halide, a hydrocarbyl substituted imidazolium halide, trialkylammonium hydrohalide or tetraalkylammonium halide of the general formulas A, B, C and D, respectively,

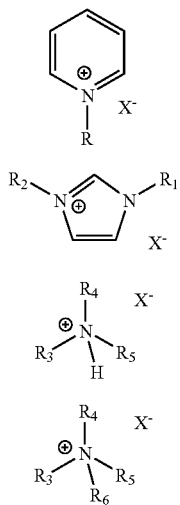

where R=H, methyl, ethyl, propyl, butyl, pentyl or hexyl group and X is a halide and preferably a chloride, and $R_1$ and $R_2$=H, methyl, ethyl, propyl, butyl, pentyl or hexyl group and where $R_1$ and $R_2$ may or may not be the same, and $R_3$, $R_4$, and $R_5$ and $R_6$=methyl, ethyl, propyl, butyl, pentyl or hexyl group and where $R_3$, $R_4$, $R_5$ and $R_6$ may or may not be the same.

DETAILED DESCRIPTION

The present invention relates to an alkylation process comprising contacting a hydrocarbon mixture comprising at least one olefin having from 2 to 6 carbon atoms and at least one isoparaffin having from 3 to 6 carbon atoms with a catalyst under alkylation conditions, said catalyst comprising a mixture of at least one acidic ionic liquid and at least one alkyl halide.

One component of a feedstock to the process of the present invention is at least one olefin having from 2 to 6 carbon atoms. This component may, for example, be any refinery hydrocarbon stream which contains olefins.

Another component of a feedstock to the process of the present invention is at least one isoparaffin having from 3 to 6 carbon atoms. This component may, for example, be any refinery hydrocarbon stream which contains isoparaffins.

The processes according to the present invention are not limited to any specific feedstocks and are generally applicable to the alkylation of $C_3$-$C_6$ isoparaffins with $C_2$-$C_6$ olefins from any source and in any combination.

In accordance with the present invention, a mixture of hydrocarbons as described above is contacted with a catalyst under alkylation conditions. A catalyst in accordance with the present invention comprises at least one acidic ionic liquid and at least one alkyl halide. The present process is being described and exemplified with reference certain specific ionic liquid catalysts, but such description is not intended to limit the scope of the invention. The processes described may be conducted using any acidic ionic liquid catalysts by those persons having ordinary skill based on the teachings, descriptions and examples included herein.

The specific examples used herein refer to alkylation processes using ionic liquid systems, which are amine-based cationic species mixed with aluminum chloride. In such systems, to obtain the appropriate acidity suitable for the alkylation chemistry, the ionic liquid catalyst is generally prepared to full acidity strength by mixing one molar part of the appropriate ammonium chloride with two molar parts of aluminum chloride. The catalyst exemplified for the alkylation process is a 1-alkyl-pyridinium chloroaluminate, such as 1-butyl-pyridinium heptachloroaluminate.

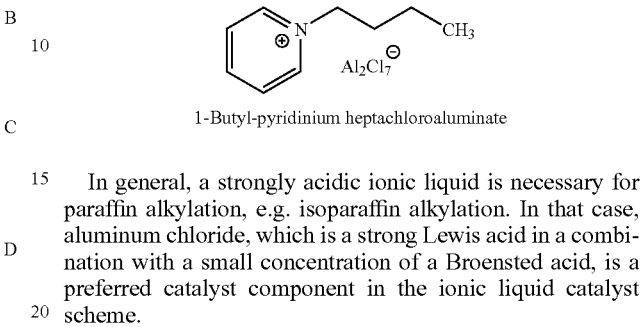

1-Butyl-pyridinium heptachloroaluminate

In general, a strongly acidic ionic liquid is necessary for paraffin alkylation, e.g. isoparaffin alkylation. In that case, aluminum chloride, which is a strong Lewis acid in a combination with a small concentration of a Broensted acid, is a preferred catalyst component in the ionic liquid catalyst scheme.

As noted above, the acidic ionic liquid may be any acidic ionic liquid. In one embodiment, the acidic ionic liquid is a chloroaluminate ionic liquid prepared by mixing aluminum trichloride ($AlCl_3$) and a hydrocarbyl substituted pyridinium halide, a hydrocarbyl substituted imidazolium halide, trialkylammonium hydrohalide or tetraalkylammonium halide of the general formulas A, B, C and D, respectively,

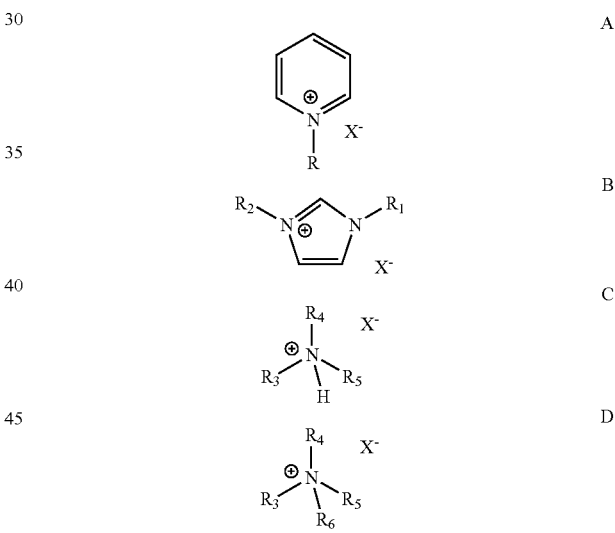

where R=H, methyl, ethyl, propyl, butyl, pentyl or hexyl group and X is a halide and preferably a chloride, and $R_1$ and $R_2$=H, methyl, ethyl, propyl, butyl, pentyl or hexyl group and where $R_1$ and $R_2$ may or may not be the same, and $R_3$, $R_4$, and $R_5$ and $R_6$=methyl, ethyl, propyl, butyl, pentyl or hexyl group and where $R_3$, $R_4$, $R_5$ and $R_6$ may or may not be the same.

The acidic ionic liquid is preferably selected from the group consisting of 1-butyl-4-methyl-pyridinium chloroaluminate, 1-butyl-pyridinium chloroaluminate, 1-butyl-3-methyl-imidazolium chloroaluminate and 1-H-pyridinium chloroaluminate.

In a process according to the invention an alkyl halide is used as a promoter. This may be done by, for example, introducing a catalytically effective amount of an appropriate alkyl halide to the reaction mixture as a component of the feed stream or by introducing it directly into the ionic liquid catalyst. The alkyl halide acts to promote the alkylation by reacting with aluminum chloride to form the prerequisite cation ions in similar fashion to the Friedel-Crafts reactions. The alkyl halides that may be used include alkyl bromides, alkyl chlorides and alkyl iodides. A variety of alkyl halides may be used, but alkyl halide derivatives of the isoparaffins or the olefins that comprise the feed streams in the alkylation process are preferable. Such alkyl halides include but are not limited to iospentyl halides, isobutyl halides, butyl halides, propyl halides and ethyl halides. Alkyl chloride versions of these alkyl halides are preferable when chloroaluminate ionic liquids are used as the catalyst systems. Other alkyl chlorides or halides having from 1 to 8 carbon atoms may be also used. The alkyl halides may be used alone or in combination.

For chloroaluminate ionic liquids, the alkyl halide is preferably an alkyl chloride such as ethyl chloride, tertiary butyl chloride, isopentyl chloride or butyl chlorides. The alkyl chlorides of choice are those derived from the isoparaffin and olefins used in a given alkylation reaction. For the alkylation of isobutane with butenes in chloroaluminate ionic liquids, for example, the preferable alkyl halides would be 1-butyl chloride, 2-butyl chloride or tertiary butyl chloride or a combination of these chlorides. Most preferably, the alkyl chloride is a derivative of the olefin stream to invoke hydride transfer and the participation for the isoparaffin. The alkyl halides are used in catalytic amounts. Ideally, the amounts of the alkyl halides should be kept at low concentrations and not exceed the molar concentration of the catalyst $AlCl_3$. The amounts of the alkyl halides used may range from 0.05 mol %-100 mol % of the Lewis acid $AlCl_3$. Concentrations of the alkyl halides in the range of 0.05 mol %-10 mol % of the $AlCl_3$ are preferable in order to keep the acidity of the catalyst at the desired performing capacity. Also, the amount of the alkyl halide should be proportional to the olefin and not exceed the molar concentration of the olefin.

Without being bound to any theory, when ethyl chloride, for example is added to acidic chloroaluminate ionic liquids, ethyl chloride reacts with $AlCl_3$ to form tetrachloroaluminate ($AlCl_4^-$) and ethyl cation. Hydride shift from the isoparaffin (isopentane or isobutane) to the generated ethyl cation leads to the tertiary cation which propagates the inclusion of the isoparaffin in the reaction and, hence, the alkylation pathway.

A metal halide may be employed to modify the catalyst activity and selectivity. The metal halides most commonly used as inhibitors/modifiers in aluminum chloride-catalyzed olefin-isoparaffin alkylations include NaCl, LiCl, KCl, $BeCl_2$, $CaCl_2$, $BaCl_2$, $SrCl_2$, $MgCl_2$, $PbCl_2$, CuCl, $ZrCl_4$ and AgCl, as described by Roebuck and Evering (Ind. Eng. Chem. Prod. Res. Develop., Vol. 9, 77, 1970). Preferred metal halides are CuCl, AgCl, $PbCl_2$, LiCl, and $ZrCl_4$.

HCl or any Broensted acid may be employed as co-catalyst to enhance the activity of the catalyst by boasting the overall acidity of the ionic liquid-based catalyst. The use of such co-catalysts and ionic liquid catalysts that are useful in practicing the present invention is disclosed in U.S. Published Patent Application Nos. 2003/0060359 and 2004/0077914. Other co-catalysts that may be used to enhance the activity include IVB metal compounds preferably IVB metal halides such as $ZrCl_4$, $ZrBr_4$, $TiCl_4$, $TiCl_3$, $TiBr_4$, $TiBr_3$, $HfCl_4$, $HfBr_4$ as described by Hirschauer et al. in U.S. Pat. No. 6,028,024.

Due to the low solubility of hydrocarbons in ionic liquids, olefins-isoparaffins alkylation, like most reactions in ionic liquids is generally biphasic and takes place at the interface in the liquid state. The catalytic alkylation reaction is generally carried out in a liquid hydrocarbon phase, in a batch system, a semi-batch system or a continuous system using one reaction stage as is usual for aliphatic alkylation. The isoparaffin and olefin can be introduced separately or as a mixture. The molar ratio between the isoparaffin and the olefin is in the range 1 to 100, for example, advantageously in the range 2 to 50, preferably in the range 2 to 20. In a semi-batch system the isoparaffin is introduced first then the olefin, or a mixture of isoparaffin and olefin. Catalyst volume in the reactor is in the range of 2 vol % to 70 vol %, preferably in the range of 5 vol % to 50 vol %. Vigorous stirring is desirable to ensure good contact between the reactants and the catalyst. The reaction temperature can be in the range −40° C. to +150° C., preferably in the range −20° C. to +100° C. The pressure can be in the range from atmospheric pressure to 8000 kPa, preferably sufficient to keep the reactants in the liquid phase. Residence time of reactants in the vessel is in the range a few seconds to hours, preferably 0.5 min to 60 min. The heat generated by the reaction can be eliminated using any of the means known to the skilled person. At the reactor outlet, the hydrocarbon phase is separated from the ionic phase by decanting, then the hydrocarbons are separated by distillation and the starting isoparaffin which has not been converted is recycled to the reactor.

Typical alkylation conditions may include a catalyst volume in the reactor of from 5 vol % to 50 vol %, a temperature of from −10° C. to +100° C., a pressure of from 300 kPa to 2500 kPa, an isopentane to olefin molar ratio of from 2 to 8 and a residence time of 5 min to 1 hour.

In one embodiment of a process according to the present invention, high quality gasoline blending components of low volatility are recovered from the alkylation zone. Those blending components are then preferably blended into gasoline.

The following Examples are illustrative of the present invention, but are not intended to limit the invention in any way beyond what is contained in the claims which follow.

EXAMPLES

Example 1

Preparation of Fresh 1-Butylpyridinium Chloroaluminate Ionic Liquid Catalyst A (Fresh IL A)

1-butyl-pyridinium chloroaluminate is a room temperature ionic liquid prepared by mixing neat 1-butyl-pyridinium chloride (a solid) with neat solid aluminum trichloride in an inert atmosphere. The syntheses of butylpyridinium chloride and the corresponding 1-butyl-pyridinium chloroaluminate are described below.

In a 2-L Teflon-lined autoclave, 400 gm (5.05 mol.) anhydrous pyridine (99.9% pure purchased from Aldrich) were mixed with 650 gm (7 mol.) 1-chlorobutane (99.5% pure purchased from Aldrich). The autoclave was sealed and the neat mixture was allowed to stir at 125° C. under autogenic pressure over night. After cooling off the autoclave and venting it, the reaction mix was diluted and dissolved in chloroform and transferred to a three liter round bottom flask. Concentration of the reaction mixture at reduced pressure on a rotary evaporator (in a hot water bath) to remove excess chloride, un-reacted pyridine and the chloroform solvent gave a tan solid product. Purification of the product was done by dissolving the obtained solids in hot acetone and precipitating the pure product through cooling and addition of diethyl ether. Filtering and drying under vacuum and heat on a rotary evaporator gave 750 gm (88% yields) of the desired product as an off-white shiny solid. $^1$H-NMR and $^{13}$C-NMR were consistent with the desired 1-butyl-pyridinium chloride and no impurities were observed.

1-butylpyridinium chloroaluminate was prepared by slowly mixing dried 1-butylpyridinium chloride and anhydrous aluminum chloride (AlCl$_3$) according to the following procedure. The 1-butylpyridinium chloride (prepared as described above) was dried under vacuum at 80° C. for 48 hours to get rid of residual water (1-butylpyridinium chloride is hydroscopic and readily absorbs water from exposure to air). Five hundred grams (2.91 mol.) of the dried 1-butylpyridinium chloride were transferred to a 2-Liter beaker in a nitrogen atmosphere in a glove box. Then, 777.4 gm (5.83 mol.) of anhydrous powdered AlCl$_3$ (99.99% from Aldrich) were added in small portions (while stirring) to control the temperature of the highly exothermic reaction. Once all the AlCl$_3$ was added, the resulting amber-looking liquid was left to gently stir overnight in the glove box. The liquid was then filtered to remove any un-dissolved AlCl$_3$. The resulting acidic 1-butyl-pyridinium chloroaluminate was used as the catalyst for the alkylation of isopentane with ethylene.

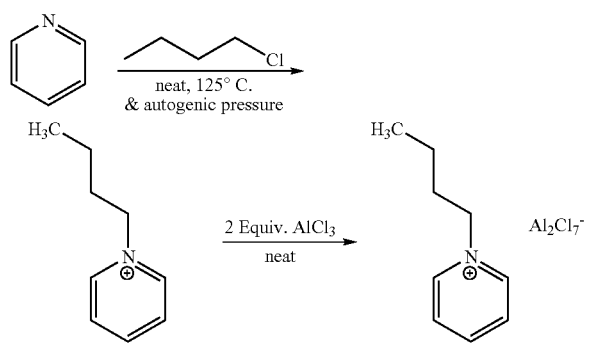

Example 2

Alkylation of isoPentane with Ethylene Without the Presence of a Promoter

A 300 cc autoclave was charged with 40 gm of ionic liquid catalyst, 100 gm anhydrous isopentane and 10 gm ethylene. The reaction was then stirred at ~1200 rpm and heated to 50° C. at autogenic pressures. The starting pressure was 288 psi. The reaction was allowed to run until the pressure dropped down into the single digits range (5 psi in this case after 28 minutes reaction time). In the case of slow going reaction, the reaction was allowed to run for 1 hr long. At the end of the reaction, the reactor was vented out and a gas sample was checked by GC for ethylene concentration. The liquid reaction mixture was allowed to settle into 2 phases. The organic phase was decanted and analyzed for product distribution by GC analysis. The reaction results are shown in Table 1.

Example 3

Alkylation of isoPentane with Ethylene in the Presence of HCl as Co-catalyst

Table 1 below shows the results of the alkylation of ethylene with isopentane in the presence of ethyl chloride and in the presence of iospentyl chloride. The alkylation of isopentane with ethylene was done according to the following procedure.

A 300 cc autoclave was charged with 40 gm of ionic liquid catalyst, 100 gm anhydrous isopentane, 10 gm ethylene, and 0.35 gm of anhydrous HCl. The reaction was then stirred at ~1200 rpm and heated to 50° C. at autogenic pressures. The starting pressure was 320 psi. The reaction was allowed to run until the pressure dropped down into the single digits range (9 psi in this case after 4 minutes reaction time). In the case of slow going reaction, the reaction was allowed to run for 1 hr long. At the end of the reaction, the reactor was vented out and a gas sample was checked by GC for ethylene concentration. The liquid reaction mixture was allowed to settle into 2 phases. The organic phase was decanted and analyzed for product distribution by GC analysis. The reaction results are shown in Table 1.

Example 4

Alkylation of isoPentane with Ethylene in the Presence of Chloroethane as a Promoter The reaction described in Example 3 was repeated but chloroethane (CH$_3$CH$_2$Cl) was added in place of hydrochloric acid (HCl). The reaction was run on 100 gm isopentane, 10 gm ethylene and 0.9 gm chloroethane in 40 gm 1-butylpyridinium chloroaluminate ionic liquid catalyst. The use of chloroethane was as effective as using HCl in the reaction. Table 1 summarizes the reaction results and conditions.

Example 5

Alkylation of Isopentane with Ethylene in the Presence of 2-Chloro-2-methylButane (Iospentyl Chloride) as Promoter The reaction described in Example 4 was repeated but iospentyl chloride was added in place of chloroethane. The reaction was run on 100 gm isopentane, 10 gm ethylene and 1.2 gm of iospentyl chloride in 40 gm 1-butylpyridinium chloroaluminate ionic liquid catalyst. Isopentyl chloride appeared to be more effective than chloroethane and HCl in the alkylation of isopentane with ethylene. The reaction was extremely exothermic and there was no need to raise the reaction temperature to 50° C. (reaction temperature). The pressure dropped instantaneously to the single digit mark from starting pressure of 337 psi. Table 1 summarizes the reaction results and conditions.

As shown in Table 1, when ethyl chloride or iospentyl chloride was added, the reaction time was noticeably shortened. The alkylation in the presence of iospentyl chloride was much quicker (almost instantaneous). The reactions were highly exothermic and there was no need to heat them up. The experimental results clearly indicate the very profound effect the addition of alkyl chlorides has on the progress of alkylations in ionic liquids.

TABLE 1

|  | No HCl or R—Cl | W/HCl | W/Ethyl-Cl | W/Iospentyl-Cl |
| --- | --- | --- | --- | --- |
| Start Pressure | 288 psig | 240 psig | 331 psig | 337 psig |
| End Pressure | 5 psig | 11 psig | 9 psig | 7 |
| ReactionTime | 28 min | 4 min. | 6 min. | 2 min. |
| % Selectivity |  |  |  |  |
| C3− | 0.04 | 0 | 0.01 | 0 |
| C4 | 0.86 | 1.88 | 1.93 | 4.97 |
| C5 | 67.78 | 67.7 | 62.79 | 65.53 |
| C6 | 1.14 | 2.6 | 2.44 | 5.19 |
| C7 | 22.33 | 19.32 | 22.53 | 14.78 |
| C8 | 2.94 | 3.25 | 3.68 | 3.27 |

TABLE 1-continued

| | No HCl or R—Cl | W/HCl | W/Ethyl-Cl | W/Iospentyl-Cl |
|---|---|---|---|---|
| C9 | 2.41 | 2.12 | 2.93 | 2.65 |
| C10 | 1.5 | 1.59 | 1.78 | 1.64 |
| C11 | 0.5 | 0.8 | 0.93 | 0.95 |
| C12+ | 0.5 | 0.75 | 0.98 | 1.02 |
| Total | 100 | 100 | 100 | 100 |

The alkylations in the previous Examples were done using pure isopentane feeds. Table 2 shows a comparison between different catalyst schemes in the alkylation of refinery pentanes with ethylene using HCl, water or ethyl chloride as promoters. Analysis of the refinery pentanes showed the feed stock to contain 86.4% iso-pentane, 8% n-pentane, 0.9% n-butane, 3.4% $C_6s$-$C_9s$ and 0.2% olefins ($C_4$ and $C_5$ olefins). The refinery pentane steam also contained 88 ppm sulfur (as mercaptans) and 0.4 ppm nitrogen. The reactions were done as described in Examples 6, 7, 8 and 9.

Example 6

Alkylation of Refinery Pentanes with Ethylene in 1-Butylpyridinium Chloroaluminate—No Promoters The refinery isopentane feed with specs described earlier was dried with over a molecular sieve to remove any residual water. Then, 101 gm of the dried feed was with 10 gm of pure ethylene in 42 gm ionic liquid catalyst according to the procedure described in Example 1. Table 2 summarizes the reaction and the results.

Example 7

Alkylation of Refinery Pentanes with Ethylene in 1-Butylpyridinium Chloroaluminate—With HCl as Promoter Using the procedure described in Example 3, dried 101 gm of refinery isopentane feed with the specs described earlier was alkylated with 10 gm of pure ethylene in 42 gm ionic liquid catalyst in the presence of 0.6 gm HCl. Table 2 summarizes the reaction and the results.

Example 8

Alkylation of Refinery Pentanes with Ethylene in 1-Butylpyridinium Chloroaluminate—With $H_2O$ as Promoter Using the procedure described in Example 3, 101 gm of the dried refinery isopentane feed with the specs described earlier was alkylated with 10 gm of pure ethylene in 42 gm ionic liquid catalyst 0.1 gm water. Table 2 summarizes the reaction and the results.

Example 9

Alkylation of Refinery Pentanes with Ethylene in 1-Butylpyridinium Chloroaluminate—With Ethyl Chloride as Promoter Using the procedure described in Example 3, 101 gm of the dried refinery isopentane feed with the specs described earlier was alkylated with 10 gm of pure ethylene in 42 gm ionic liquid catalyst 1 gm of ethyl chloride. Table 2 summarizes the reaction and the results.

Table 2 summarizes the results of alkylations of refinery isopentane feed with pure ethylene described in Examples 6, 7, 8 and 9.

TABLE 2

| | (Alkylation of Refinery Feed in Butylpyridinium Chloride-2AlCl₃/EtCl) | | | |
|---|---|---|---|---|
| | Ref. Feed No HCl or R—Cl | Ref feed W/HCl | Ref Feed W/Ethyl-Cl | Ref Feed W/H2O |
| Start Pressure | 226 psi | 249 psi | 295 psig | 313 psi |
| End Pressure | 104 psi | 10 psi | 13 psig | 15 psi |
| Reaction Time | 64 min. | 19 min. | 24 min. | 28 min. |
| % Selectivity. | | | | |
| C3– | 0.21 | 0.07 | 0.05 | 0.19 |
| C4 | 0.77 | 1.19 | 1.39 | 1.27 |
| C5 | 81.34 | 69.35 | 62.69 | 68.93 |
| C6 | 2.82 | 3.06 | 3.87 | 2.97 |
| C7 | 8.74 | 18.36 | 21.03 | 18.18 |
| C8 | 3 | 3.8 | 5.05 | 3.93 |
| C9 | 1.41 | 2.02 | 2.55 | 2.14 |
| C10 | 0.82 | 1.26 | 1.70 | 1.24 |
| C11 | 0.37 | 0.42 | 0.83 | 0.53 |
| C12+ | 0.53 | 0.48 | 0.84 | 0.61 |
| Total | 100 | 100 | 100 | 100 |

There are numerous variations on the present invention which are possible in light of the teachings and supporting examples described herein. It is therefore understood that within the scope of the following claims, the invention may be practiced otherwise than as specifically described or exemplified herein.

What is claimed is:

1. An alkylation process comprising contacting a hydrocarbon mixture comprising at least one olefin having from 2 to 6 carbon atoms and at least one isoparaffin having from 3 to 6 carbon atoms under alkylation conditions including an isopentane to olefin molar ratio of from 2 to 8, in the presence of an acidic ionic liquid catalyst in an alkylation zone, said catalyst comprising a mixture of at least one acidic ionic liquid and at least one alkyl halide; wherein the at least one olefin and the at least one isoparaffin are alkylated; and where the acidic ionic liquid is a chloroaluminate ionic liquid prepared by mixing aluminum trichloride ($AlCl_3$) and a hydrocarbyl substituted pyridinium halide, a hydrocarbyl substituted imidazolium halide, trialkylammonium hydrohalide or tetraalkylammonium halide of the general formulas A, B, C and D, respectively,

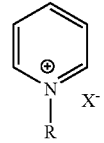

A

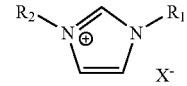

B

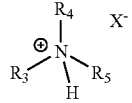

C

-continued

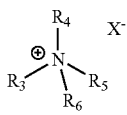

where R=H, methyl, ethyl, propyl, butyl, pentyl or hexyl group and X is a halide, and $R_1$ and $R_2$=H, methyl, ethyl, propyl, butyl, pentyl or hexyl group and where $R_1$ and $R_2$ may or may not be the same, and $R_3$, $R_4$, and $R_5$ and $R_6$=methyl, ethyl, propyl, butyl, pentyl or hexyl group and where $R_3$, $R_4$, $R_5$ and $R_6$ may or may not be the same.

2. The process according to claim 1, wherein the acidic ionic liquid is selected from the group consisting of 1-butyl-4-methyl-pyridinium chloroaluminate (BMP), 1-butyl-pyridinium chloroaluminate (BP), 1-butyl-3-methyl-imidazolium chloroaluminate BMIM) and 1-H-pyridinium chloroaluminate (HP).

3. The process according to claim 1, wherein the acidic ionic liquid is selected from the group consisting of 1-butyl-4-methyl-pyridinium chloroaluminate (BMP), 1-butyl-pyridinium chloroaluminate (BP), and 1-H-pyridinium chloroaluminate (HP).

4. An alkylation process comprising contacting a hydrocarbon mixture comprising at least one olefin having from 2 to 6 carbon atoms and at least one isoparaffin having from 3 to 6 carbon atoms under alkylation conditions in the presence of an acidic ionic liquid catalyst in an alkylation zone, said catalyst comprising a mixture of at least one acidic ionic liquid and at least one alkyl halide; where the acidic ionic liquid is a chloroaluminate ionic liquid prepared by mixing aluminum trichioride ($AlCl_3$) and a hydrocarbyl substituted pyridinium halide having the general formula A:

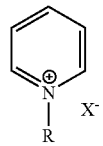

where R=H, methyl, ethyl, propyl, butyl, pentyl or hexyl group and X is a halide; and wherein the isoparaffin and the ethylene are alkylated.

5. The alkylation process of claim 4, wherein the alkylation conditions include an isopentane to olefin molar ratio of from 2 to 8.

6. The process according to claim 1 or claim 4, wherein the catalyst further comprises an HCl co-catalyst.

7. The process according to claim 1 or claim 4, wherein the isoparaffin is selected from the group consisting of isobutane, isopentanes and mixtures thereof.

8. The process according to claim 1 or claim 4, wherein the olefin is selected from the group consisting of ethylene, propylene, butylenes, pentenes and mixtures thereof.

9. The process according to claim 1 or claim 4, wherein the alkylation conditions include a catalyst volume in the reactor of from 5 vol % to 50 vol %, a temperature of from −10° C. to 100° C., a pressure of from 300 kPA to 2500 kPa, and a residence time of 1 minute to 1 hour.

10. The process according to claim 1 or claim 4, further comprising recovering high quality gasoline blending components of low volatility from the alkylation zone.

11. The process according to claim 10, further comprising blending said components into gasoline.

12. The process according to claim 1 or claim 4, wherein the alkyl halide has from 1 to 8 carbon atoms.

13. The process according to claim 12, where the alkyl halide is selected from the group consisting of methyl halide, ethyl halide, propyl halide, 1-butyl halide, 2-butyl halide, tertiary butyl halide, pentyl halides, iospentyl halide, hexyl halides, isohexyl halides, heptyl halides, isoheptyl halides, octyl halides and isooctyl halides.

14. The process according to claim 12, where the alkyl halide is selected from the group consisting of alkyl bromides, alkyl iodides, and alkyl chlorides.

15. Thealkylation process of claim 1 or claim 4, wherein the halide is chloride.

* * * * *